(12) United States Patent
Landes

(10) Patent No.: US 12,386,170 B2
(45) Date of Patent: Aug. 12, 2025

(54) ILLUMINATION DEVICE FOR AN ENDOSCOPE

(71) Applicant: HOYA CORPORATION, Tokyo (JP)

(72) Inventor: Hermann Landes, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 180 days.

(21) Appl. No.: 18/023,510

(22) PCT Filed: Aug. 19, 2021

(86) PCT No.: PCT/IB2021/057629
§ 371 (c)(1),
(2) Date: Feb. 27, 2023

(87) PCT Pub. No.: WO2022/043835
PCT Pub. Date: Mar. 3, 2022

(65) Prior Publication Data
US 2023/0333363 A1 Oct. 19, 2023

(30) Foreign Application Priority Data
Aug. 31, 2020 (DE) ...................... 10 2020 122 636.5

(51) Int. Cl.
G02B 23/24 (2006.01)
G06V 10/14 (2022.01)
(52) U.S. Cl.
CPC ....... *G02B 23/2461* (2013.01); *G02B 23/243* (2013.01); *G06V 10/14* (2022.01); *G06T 2207/10068* (2013.01)
(58) Field of Classification Search
None
See application file for complete search history.

(56) References Cited

U.S. PATENT DOCUMENTS 7,922,655 B2 * 4/2011 Yasushi .............. A61B 1/00181
600/173
2001/0003142 A1 6/2001 Koshikawa
(Continued)

FOREIGN PATENT DOCUMENTS

CN 101129255 A 2/2008
CN 101144972 A 3/2008
(Continued)

OTHER PUBLICATIONS

STIC provided translation of Sasaki (JP 2012-205619 A referred to as "Sasaki" throughout) (Year: 2012).*
(Continued)

*Primary Examiner* — Tyler W. Sullivan
(74) *Attorney, Agent, or Firm* — GREENBLUM & BERNSTEIN, P.L.C.

(57) ABSTRACT

An endoscope tip having an objective for imaging a field of view, and further having an illumination device for illuminating the field of view. The objective has an angle of view greater than 180°, the illumination device is arranged around the objective, and the illumination device includes a transparent cap from which the illumination light is emitted into the field of view. The illumination device further includes one or more light emitting devices that emit emission light, and for one of the light emitting devices, a centroid of an angular distribution of the emission light is located in a direction tilted away from the optical axis, or a reflective surface reflects at least the emission light in a direction further away from the direction of the optical axis than a direction in which the emission light is incident on the reflective surface.

13 Claims, 12 Drawing Sheets

(56) References Cited

U.S. PATENT DOCUMENTS

| | | |
|---|---|---|
| 2008/0045797 A1 | 2/2008 | Yagi et al. |
| 2008/0045798 A1 | 2/2008 | Fukuhori |
| 2008/0070132 A1 | 3/2008 | Hashimoto et al. |
| 2009/0069633 A1 | 3/2009 | Orihara et al. |
| 2010/0312057 A1* | 12/2010 | Konno .................. A61B 1/07 600/162 |
| 2011/0157574 A1 | 6/2011 | Kato et al. |
| 2014/0357948 A1 | 12/2014 | Kikuchi et al. |
| 2016/0100750 A1 | 4/2016 | Furuta |
| 2017/0215714 A1 | 8/2017 | Shinji et al. |
| 2018/0140361 A1* | 5/2018 | Sinha .................. A61B 1/233 |
| 2018/0256014 A1 | 9/2018 | Shinji et al. |
| 2019/0082085 A1 | 3/2019 | Oka |
| 2019/0167085 A1 | 6/2019 | Wilson |
| 2021/0007591 A1 | 1/2021 | Weber et al. |
| 2021/0068863 A1* | 3/2021 | Choi .................. A61B 5/395 |

FOREIGN PATENT DOCUMENTS

| | | | |
|---|---|---|---|
| CN | 101380219 A | 3/2009 | |
| CN | 102316783 A | 1/2012 | |
| CN | 107105965 A | 8/2017 | |
| CN | 109770822 A | 5/2019 | |
| DE | 10 2018 202243 A1 | 8/2019 | |
| EP | 1769718 A1 | 4/2007 | |
| EP | 3767363 A1 | 1/2021 | |
| JP | 2005-342299 A | 12/2005 | |
| JP | 4782900 B2 * | 9/2011 | ......... A61B 1/00045 |
| JP | 2012-055561 A | 3/2012 | |
| JP | 2012-157577 A | 8/2012 | |
| JP | 2012-205619 A | 10/2012 | |
| JP | 2013-236665 A | 11/2013 | |
| JP | 2015-016020 A | 1/2015 | |
| JP | 2015-112389 A | 6/2015 | |
| WO | WO2006/004083 A1 | 4/2008 | |
| WO | WO2010/113550 A1 | 10/2012 | |
| WO | WO2017/094165 A1 | 6/2017 | |
| WO | WO2017/179168 A1 | 10/2017 | |
| WO | WO2019/158168 A1 | 8/2019 | |

OTHER PUBLICATIONS

STIC provided translation of Keishi, et al. (JP2015-112389 A referred to as "Keishi" throughout) (Year: 2015).*

STIC Provided Translated of JP 4782900 B2 (Year: 2011).*

International Search Report issued in International Bureau of WIPO Patent Application No. PCT/IB2021/057629, dated Nov. 22, 2021, along with an English translation thereof.

Written Opinion of the International Searching Authority issued in International Bureau of WIPO Patent Application No. PCT/IB2021/057629, dated Nov. 22, 2021, along with an English translation thereof.

Office Action issued in Japanese Patent Application No. 2023-513804, dated Jun. 11, 2024, along with an English translation thereof.

International Search Report issued in Japanese Patent Application No. 2023-513804, dated Mar. 5, 2024, along with an English translation thereof.

Office Action issued in family member Japanese Patent Application No. 2024-121329, dated Jan. 7, 2025, along with an English translation thereof.

Office Action issued in Chinese Patent Application No. 202180053329.2, dated May 30, 2025, along with an English translation thereof.

* cited by examiner

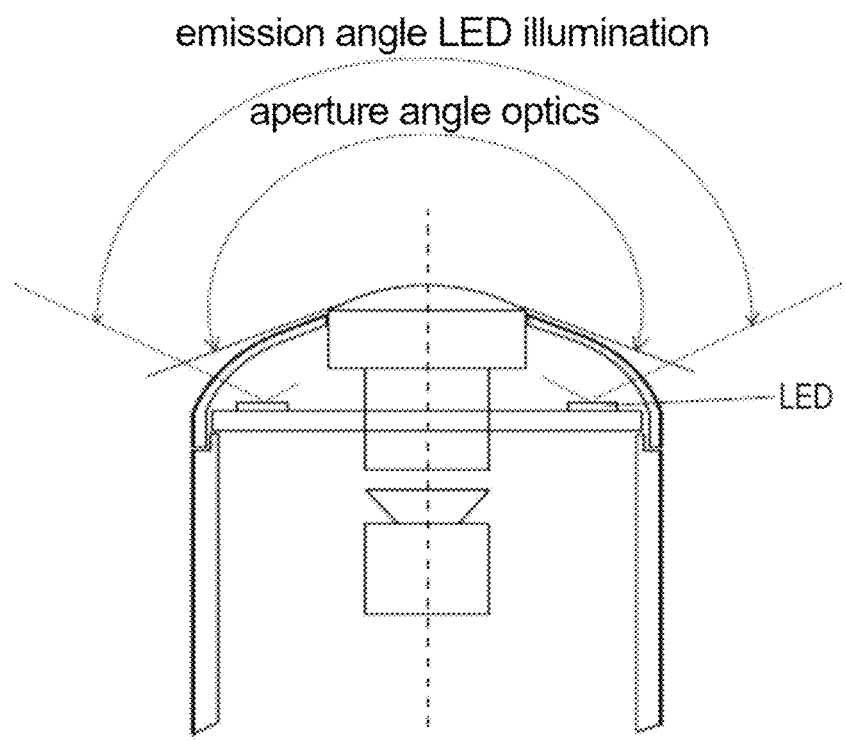
Fig. 6
PRIOR ART
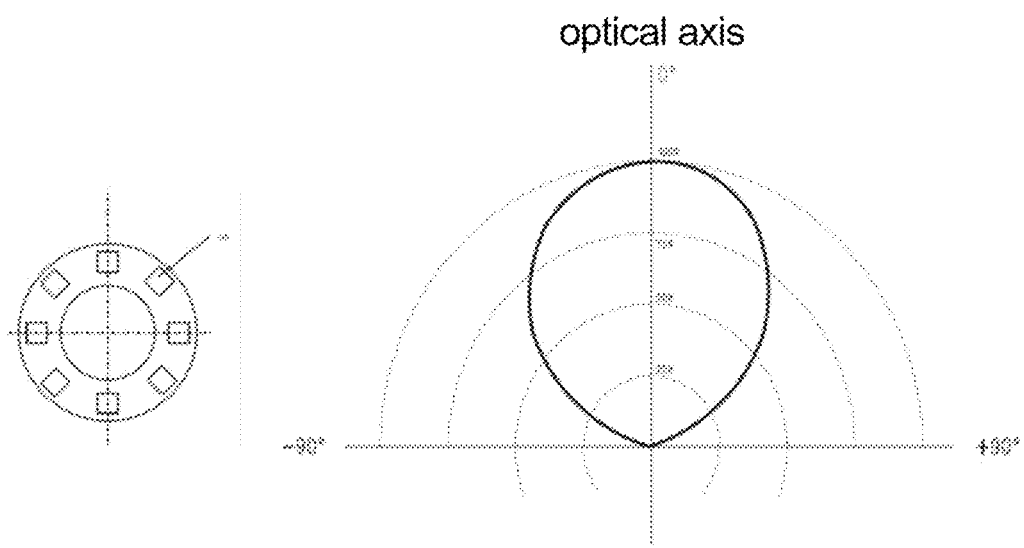
Fig. 7
PRIOR ART
Fig. 8
PRIOR ART endoscope tip

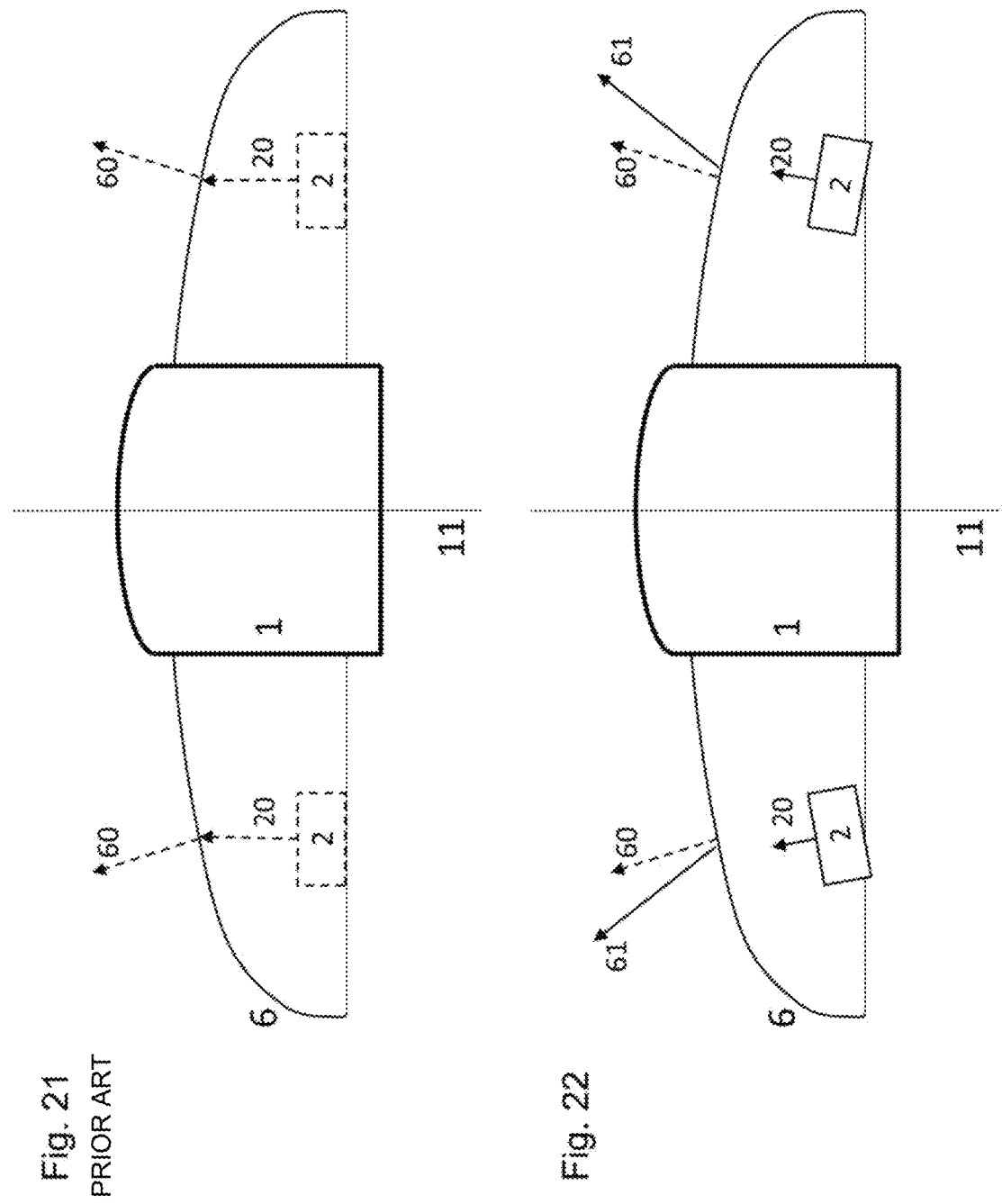

ILLUMINATION DEVICE FOR AN ENDOSCOPE

The present invention relates to an illumination device for an endoscope. In particular, it relates to an illumination device for an endoscope with an objective having a large angle of view, in particular an angle of view greater than 180°.

PRIOR ART

The illumination system of an endoscope can include a plurality of LEDs arranged around an objective. The light emitting devices are typically arranged in a plane perpendicular to the optical axis of the objective, and the light emitting devices are configured to emit light parallel to the optical axis. More precisely, the centroid of the angular distribution of the emission is located in the direction of the optical axis. The light of the LEDs passes through a transparent cap and then illuminates the field of view. The transparent cap delimits the illumination device towards the object space containing the field of view of the objective.

Technical Problem

It is desirable that the field of view of an objective of an endoscope with an imaging system is illuminated as homogeneously as possible, as shown in FIG. 1 by the hatched area for an angle of view of 180°. If the objective has an angle of view greater than 180° and the LEDs are Lambertian emitters which emit their light directly onto the transparent cap in the direction of the optical axis, a more or less homogeneous illumination of the field of view cannot be achieved, as shown in FIG. 2. In FIG. 2, the solid line indicates the radiation field of the Lambertian emitter.

Solution to the Problem

It is provided: An endoscope tip or a capsule endoscope with
- an objective for imaging a field of view; and
- an illumination device for illuminating the field of view with illumination light, wherein
- the objective has an optical axis;
- the objective has an angle of view greater than 180°;
- the illumination device is arranged around the objective in a plan view along the optical axis;
- the illumination device includes a transparent cap from which the illumination light is emitted into the field of view;
- the illumination device includes one or more light emitting devices configured to emit respective emission light from a respective light emitting surface; and
- the illumination device satisfies at least one of the following conditions:
  - at least one of the light emitting devices is configured such that a centroid of an angular distribution of the respective emission light is located in a direction tilted away from the optical axis by an angle greater than or equal to 5° and less than or equal to 85°; and
  - the illumination device includes a reflective surface that reflects at least a part of one of the emission lights in a direction further away from the direction of the optical axis than a direction in which the part of the one of the emission lights is incident on the reflective surface.

Advantages of the Solution

A more or less homogeneous illumination of the field of view of the objective is achieved by the illumination device even if it has an angle of view greater than 180°. "More or less homogeneous" means that the light intensity over the entire angle of view is between 50% and 100% of the maximum light intensity (preferably between 75% and 100% of the maximum light intensity). Some examples are additionally relatively simple and space-saving. Optically refractive components can be dispensed with in some cases (if a possibly minimal refraction at the transparent cap is neglected), which makes the production simple and thus cost-effective.

BRIEF DESCRIPTION OF THE DRAWINGS

FIG. 6 compares the angle of view of the objective with the emission angle of the illumination in the endoscope tip of FIG. 4;

FIG. 7 shows a plan view of the LEDs of the endoscope tip of FIG. 4;

FIG. 8 shows a radiation pattern for the endoscope tip of FIG. 4;

FIG. 21 shows a reference configuration for explaining a principle of the examples of the invention; and FIG. 22 shows an example of the invention for explaining the principle of the examples of the invention.

DETAILED DESCRIPTION OF EXAMPLES

Figure 3:
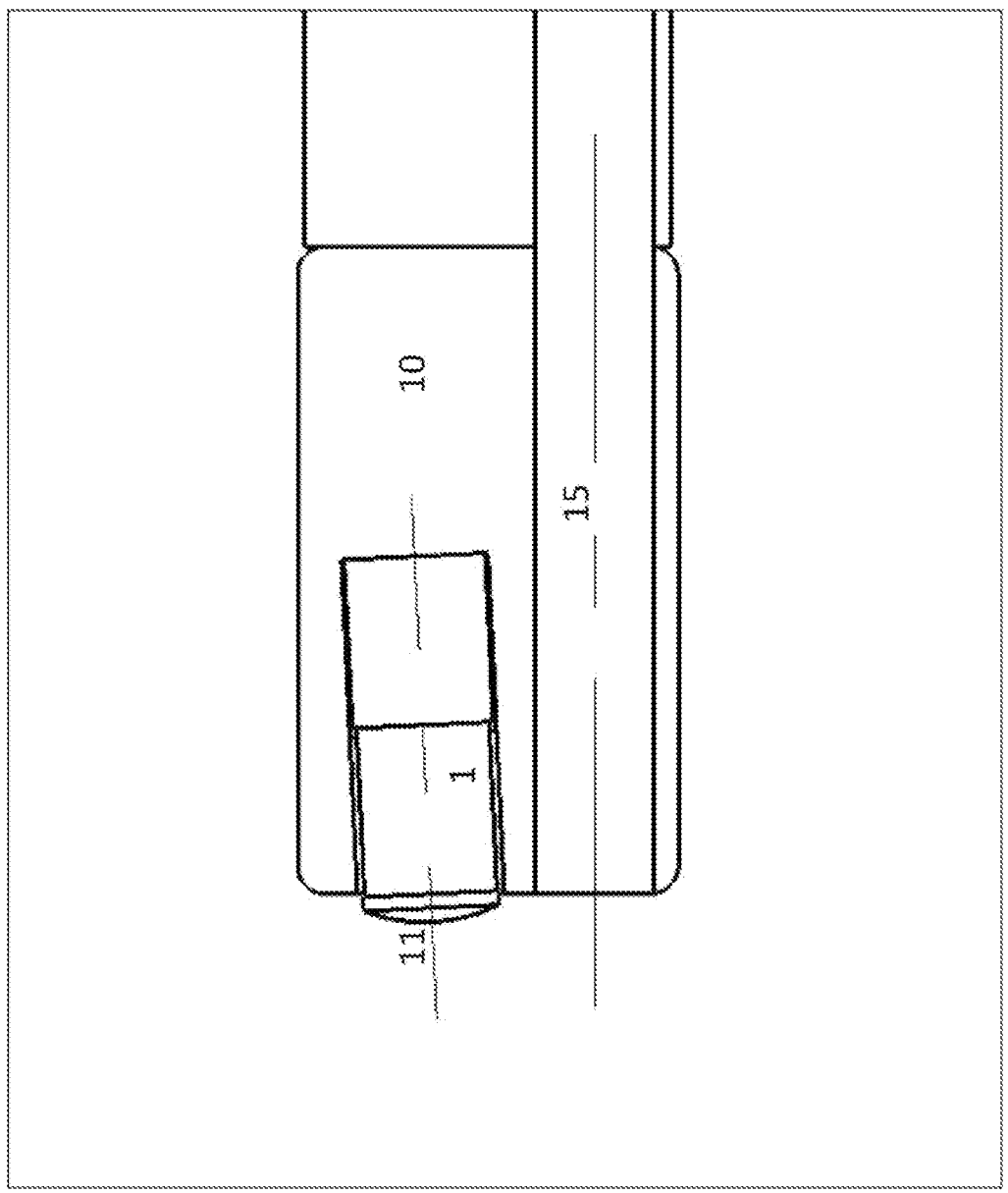
FIG. 3 shows an endoscope tip with an objective, in which the illumination device according to an example of the invention can be mounted.

FIG. 3 shows an example of an endoscope tip 10 in which an objective 1 (preferably a wide-angle objective with an angle of view of more than 180°) is arranged. The optical axis 11 of the objective 1 can extend parallel to the axis of symmetry 15 of the endoscope tip 10. In particular, the optical axis 11 of the objective 1 can be identical to the axis of symmetry 15 of the endoscope tip 10 or can be offset therefrom. However, the optical axis 11 can also be inclined with respect to the axis of symmetry 15 of the endoscope tip 10, as shown in the example of FIG. 3.

The illumination device is mounted around the objective 1 in a plan view of the distal end of the endoscope tip. It can be mounted, for example, directly around the objective 1 or can be spaced apart from the objective 1. The illumination device can be rotationally symmetric. If the illumination device is rotationally symmetric, its rotation axis is preferably (but not necessarily) identical to the optical axis 11 of the objective 1.

In the following, the invention is explained with reference to an endoscope tip 10, in which the objective 1 is mounted symmetrically to the axis of the endoscope tip 10 and the illumination is mounted rotationally symmetric about the optical axis of the objective 1. However, the invention is not limited to this particular configuration, as explained above.

Figure 4:
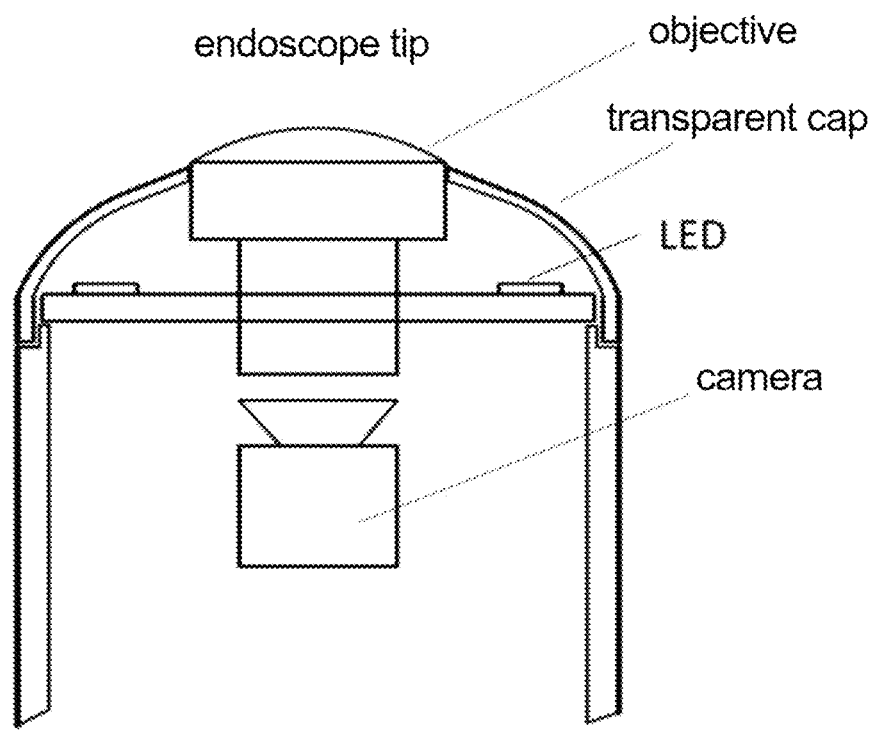
FIG. 4 shows an endoscope tip according to the prior art.
Figure 5:
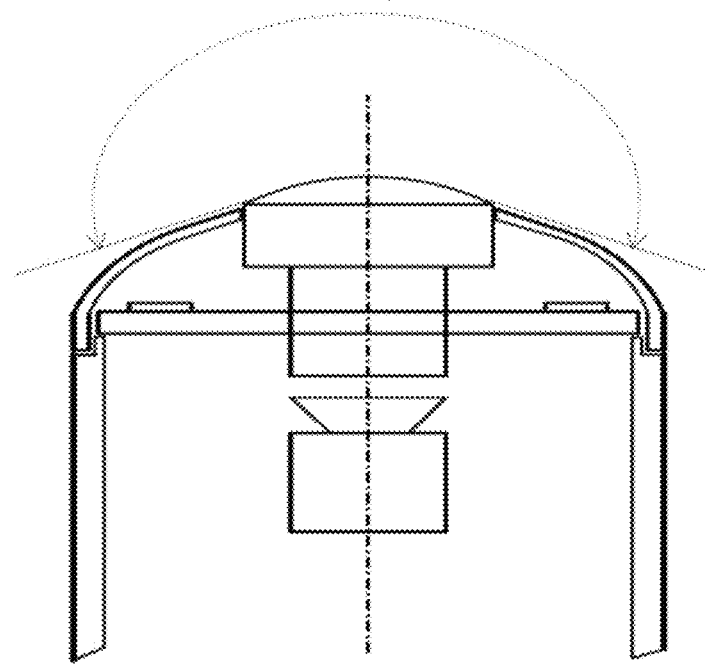
FIG. 5 illustrates the angle of view of the objective located in the endoscope tip of FIG. 4.

FIG. 4 shows an endoscope tip according to the prior art. An objective with an angle of view of more than 180° is located in the endoscope tip. The angle of view ("aperture angle optics") is illustrated in FIG. 5. Due to the large aperture angle of the optics, the objective should be located at the tip of the endoscope and all other parts (endoscope cap, illumination) are set back behind it so as not to appear in the field of view.

The endoscope tip may further include a camera to capture the image of the field of view captured by the objective. The camera may have, for example, a CCD chip or CMOS chip as a sensor. Instead of the camera, the endoscope tip may also include a part of a relay optics guiding the image captured by the objective to the proximal end of the endoscope. The endoscope tip further includes an illumination device (also referred to as a "light") to illuminate the field of view of the objective (or the object space containing the field of view). LEDs are mounted in the illumination device which illuminate the object space through a transparent cap (endoscope cap). The cap is transparent if its transparency is at least 75%, preferably at least 90%, and more preferably at least 95% for all wavelengths emitted with an intensity of at least 50% of the maximum intensity of the LEDs as a function of the wavelength. The cap should not be tinting. That is, a transparency for different wavelengths should differ by no more than 20%, preferably by no more than 10%. If the LEDs also emit light with a wavelength outside the visible range (400 nm to 800 nm), the above conditions can be applied to the wavelengths in the visible range and not to the wavelengths outside the visible range.

The refractive power of the cap is typically small, since it acts essentially like a plane-parallel plate. The refractive power can be locally different. For example, the maximum local refractive power can be 2 dpt (2 m$^{-1}$), preferably 1 dpt (1 m$^{-1}$), and even more preferably 0.5 dpt (0.5 m$^{-1}$). However, in some examples of the invention, the cap can be configured as a lens with a refractive power to direct the illumination light into predetermined regions of the field of view.

The LEDs can all be of the same type, or of different types. For example, two different types can be used to illuminate the object space with two different colors. In this case, the LEDs of each individual type should preferably be mounted rotationally symmetric about the optical axis of the objective. An example of this is shown in FIG. 7 in plan view.

The LEDs can all be controllable individually or in groups. "Controllable" means at least that the LEDs can be switched on and off. In some examples, the intensity and/or the color of the emission light can also be controlled.

FIG. 6 shows the emission angle of the LED illumination of the endoscope tip of FIG. 4 according to the prior art. In this case, the emission angle of the LED illumination is such that the field of view of the objective is not or not sufficiently illuminated at the edges. This means that the large angle of view of the objective is (rather) useless. The emission angle indicates the range within which the intensity of the light is at least 50% of the maximum intensity (at the same distance from the LED). FIG. 8 shows a radiation pattern corresponding to FIG. 6. All radiation patterns shown are relative to the optical axis of the objective. In all radiation patterns shown, the total illumination is normalized to 0%.

Figure 9:
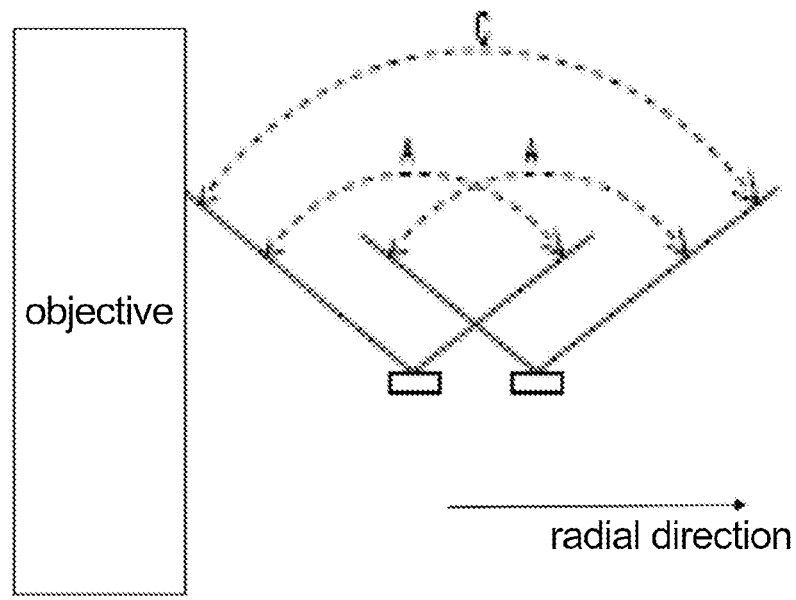
FIG. 9 shows a possible arrangement of LEDs in an endoscope tip.
Figure 10:
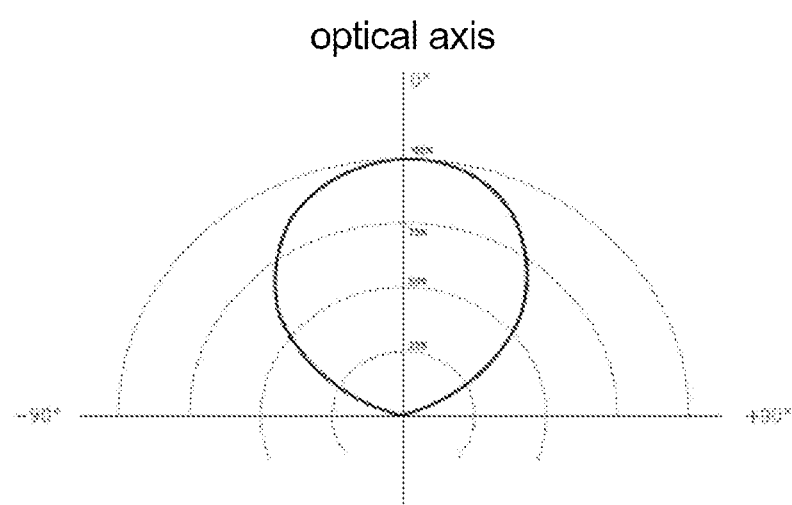
FIG. 10 shows a radiation pattern for the endoscope tip of FIG. 9.

One could try to mount a plurality of LEDs of the same type next to each other in radial direction, as shown in FIG. 9. However, the emission angle does not change thereby (C=A), so that a part of the outer field of view still remains without illumination. FIG. 10 shows the corresponding radiation pattern, which does not differ qualitatively from the radiation pattern shown in FIG. 8. In principle, the mounting of a plurality of LEDs in radial direction, each emitting parallel to the optical axis of the objective, only corresponds to an enlargement of the emission surface of an individual LED.

Figure 11:
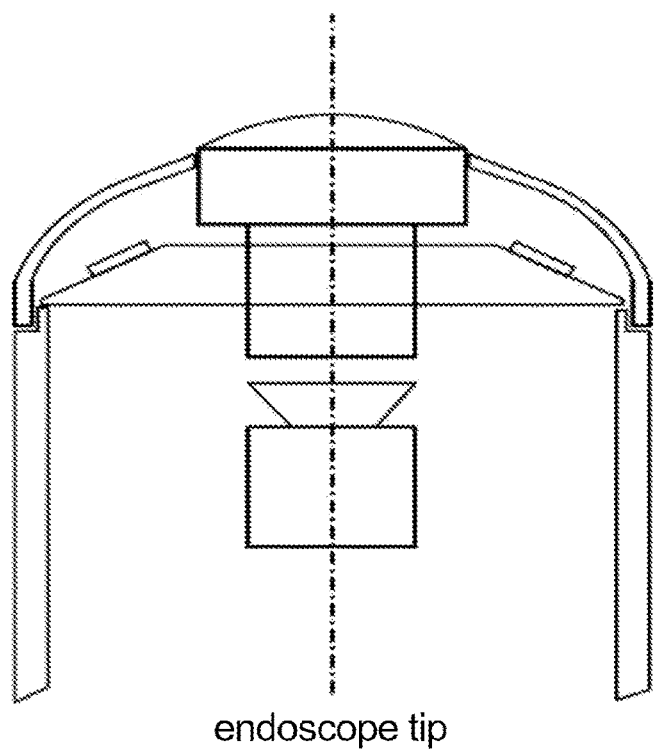
FIG. 11 shows an endoscope tip according to a first example of the invention.

FIG. 11 shows an endoscope tip according to a first example of the invention. The endoscope tip corresponds exactly to the endoscope tip of FIG. 4, except that the LEDs do not emit parallel to the optical axis of the objective, but emit at a finite angle away from it. The finite angle can be, for example, in a range from 5° to 85°, 5° to 80°, 10° to 85°, or 10° to 80°, preferably in a range from 5° to 50°, and even more preferably in a range from 10° to 45°. The finite angle is different from 0° and from 90°.

For this, the LEDs are mounted on a surface that is inclined with respect to a surface perpendicular to the optical axis. The angle of inclination of the surface corresponds to the change of the emission angle of the illumination device and can be selected according to the desired emission characteristic. The surface can be formed, for example, by a truncated cone that can be used instead of the flat mounting surface for the LEDs according to FIG. 4. Preferably (but not necessarily), the axis of the truncated cone coincides with the optical axis of the objective.

According to FIG. 11, the LEDs are also closer to the distal end due to the mounting on the truncated cone surface. However, this is not necessary. For example, instead of the truncated cone surface, troughs can also be placed in the LED mounting surface of FIG. 4, so that the center of the LED emission surface is located at the same height in the direction of the optical axis as in FIG. 4.

Figure 12:
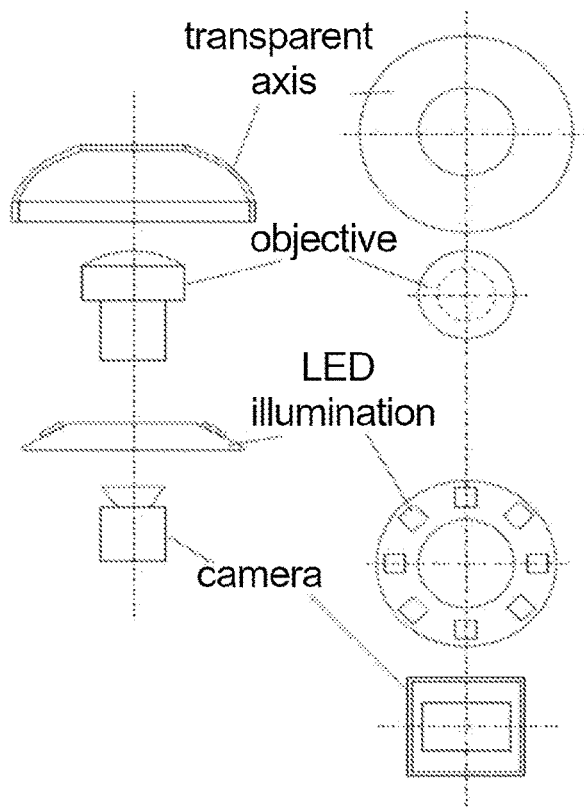
FIG. 12 shows cross-sections and plan views of components of the endoscope tip according to FIG. 11.

FIG. 12 shows the components of the endoscope tip of FIG. 11 in cross-section (left) and in plan view (right).

Figure 13:
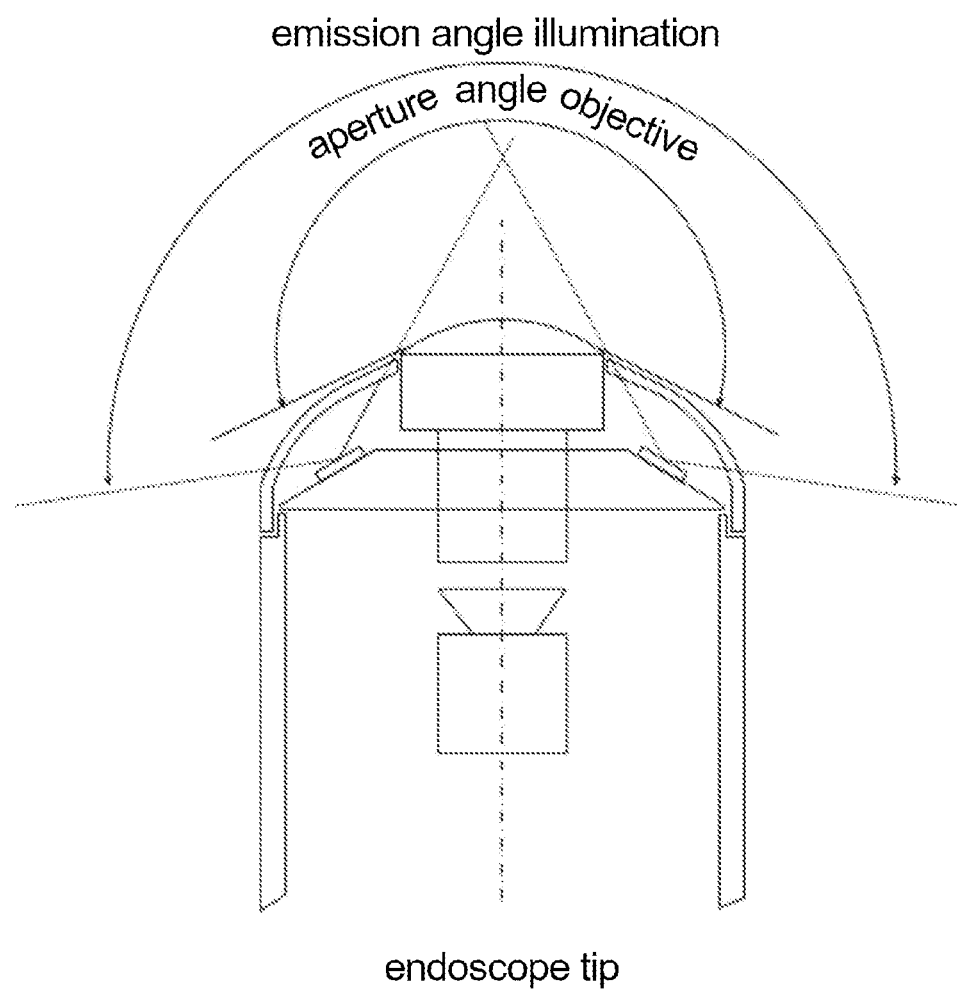
FIG. 13 compares the emission angle of the illumination and the aperture angle of the objective of the endoscope tip of FIG. 11.
Figure 14:
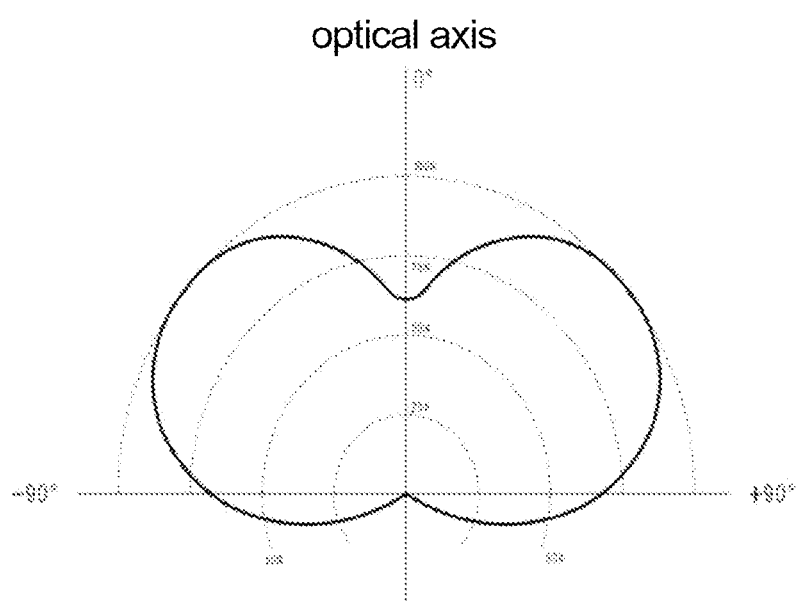
FIG. 14 shows a radiation pattern for the endoscope tip of FIG. 11.

FIG. 13 shows the emission angle of the illumination and the aperture angle of the objective of the endoscope tip of FIG. 11, corresponding to the illustration in FIG. 6. As can be seen, the outer region of the field of view of the endoscope is now substantially better illuminated. FIG. 14 shows the corresponding radiation pattern. The illumination is still sufficient even at angles of view of more than 180°.

FIGS. 15 to 18 show a second example of the invention. FIGS. 15 to 18 correspond to FIGS. 11 to 14, respectively.

Figure 17:
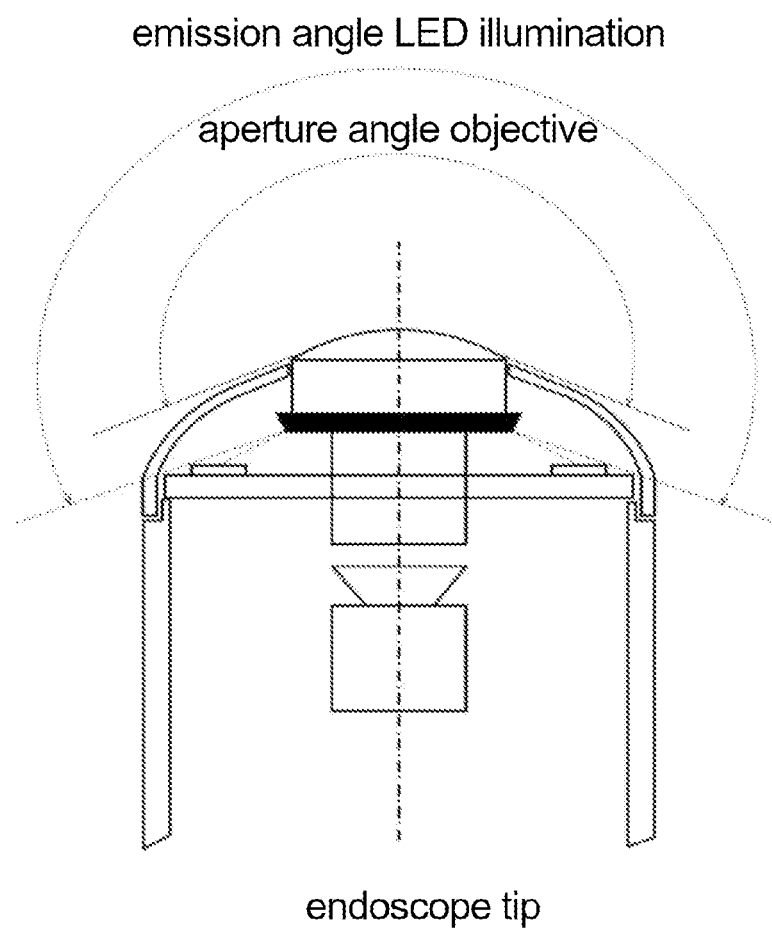
FIG. 17 compares the emission angle of the illumination and the aperture angle of the objective of the endoscope tip of FIG. 15.
Figure 18:
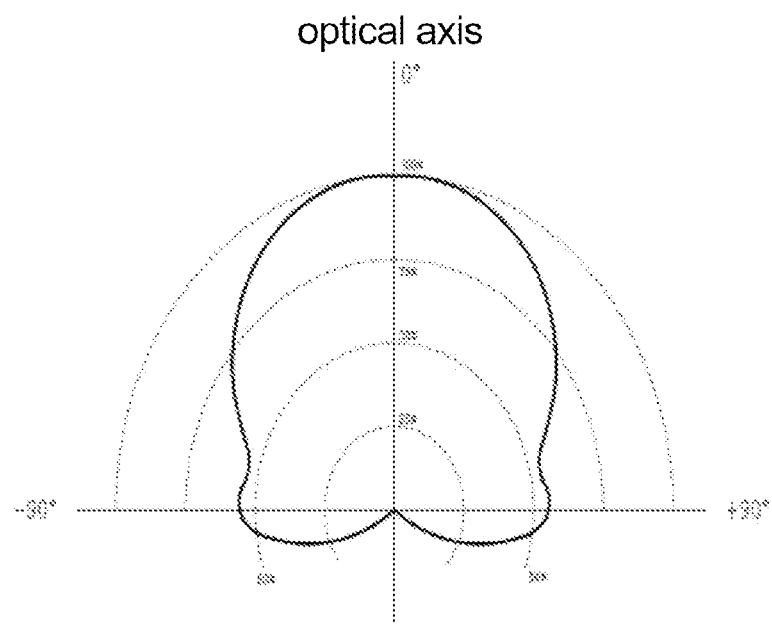
FIG. 18 shows a radiation pattern for the endoscope tip of FIG. 15.

In contrast to the first example, in the second example, the LEDs are again mounted on a plane perpendicular to the optical axis, as in FIG. 4. However, the endoscope tip has, in addition to the endoscope tip of FIG. 4, a ring mirror, which is mounted around the objective. Preferably, the ring mirror is rotationally symmetric with the optical axis of the objective as the rotation axis. The reflective surface of the ring mirror faces the LEDs and is inclined with respect to the optical axis by a finite angle. For example, the angle of inclination can be in a range of 20° to 70° relative to the optical axis. A part of the radiation is thereby reflected into the outer region of the field of view, so that a sufficient illumination is achieved there as well, and in particular also at angles of view greater than 180°, as can be seen in FIGS. 17 and 18.

The ring mirror should preferably be mounted such that it does not cause shadowing in addition to that by the objective. This means that the protrusion of the ring mirror should be determined depending on the height in the direction of the optical axis at which the ring mirror is mounted.

The ring mirror preferably reflects emission light from the LEDs, which is shadowed in the endoscope tip of FIG. 4 by the objective, and therefore does not contribute or only contributes insignificantly to the illumination of the object space. The light utilization is thereby improved, and the energy consumption and the heat generation are reduced.

Figure 19:
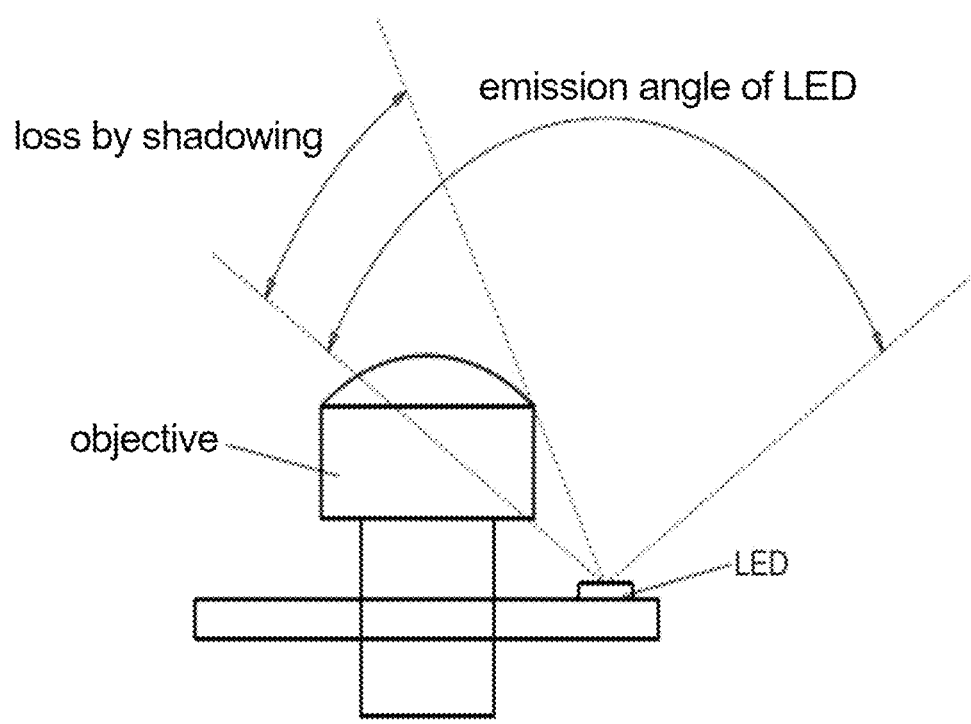
FIG. 19 shows the principle of shadowing in an endoscope tip according to the prior art.
Figure 20:
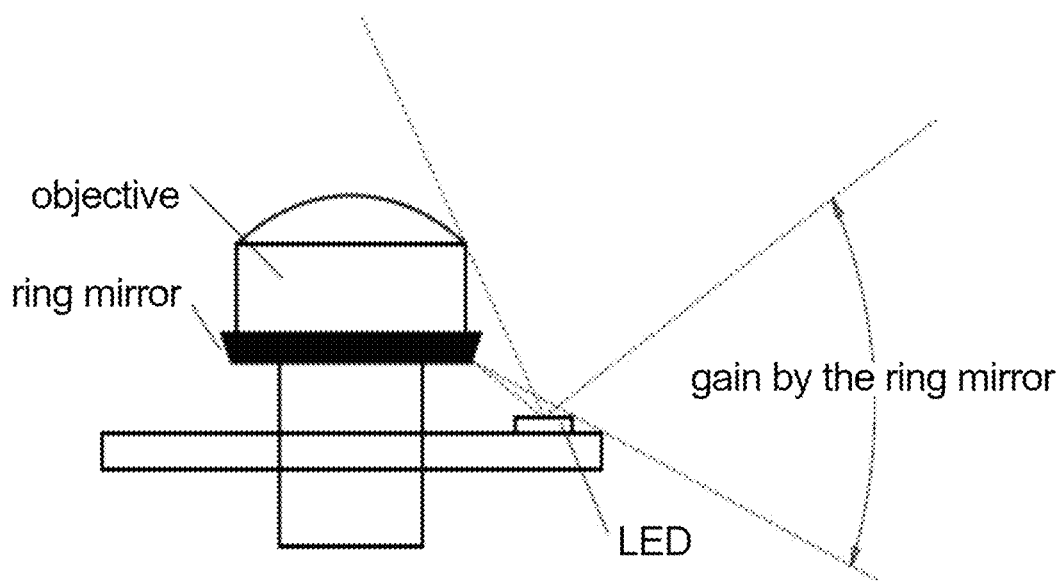
FIG. 20 shows how the shadowed light according to the second example is used for illuminating the outer field of view.

This is shown in FIGS. 19 and 20. FIG. 19 shows an endoscope tip (without the transparent cap) according to the prior art, in which a part of the emission light from the LED is shadowed by the objective. In contrast, according to the second example, the shadowed light is reflected by the ring mirror into the outer field of view, as shown in FIG. 20. The shadowing in the center does not change.

The mirror surface of the ring mirror may form a truncated cone surface, at which no optical refractive power is exerted in the direction of the optical axis. However, in some examples of the invention, it may be advantageous if the ring mirror exerts an optical refractive power in the direction of the optical axis to direct light into certain regions of the field of view. In such a case, the mirror surface is curved in the cross-sections of FIGS. 15, 16, 17 and 20. The mirror surface of the ring mirror may generally even have an arbitrary shape. Preferably (but not necessarily), the axis of the truncated cone coincides with the optical axis of the objective.

In some examples of the invention, the bottom surface of the ring mirror and at least a part of the outer shell of the objective adjoining the bottom surface of the ring mirror are additionally coated reflectively. As a result, emission light emerging from the LED with a flat angle can be directed into the outer field of view by multiple reflection at the outer shell of the objective and the bottom surface of the ring mirror. This increases the light utilization even further.

The same effect can also be achieved without the ring mirror if the outer shell of the objective has a protruding part above the LEDs in the direction of the optical axis, as for example in FIGS. 4 and 11. According to a third example of the invention, both the bottom surface of the protrusion and at least a part of the outer shell of the objective adjoining the protrusion below the protrusion are coated reflectively to direct light from the LED into the outer field of view.

Figure 1:
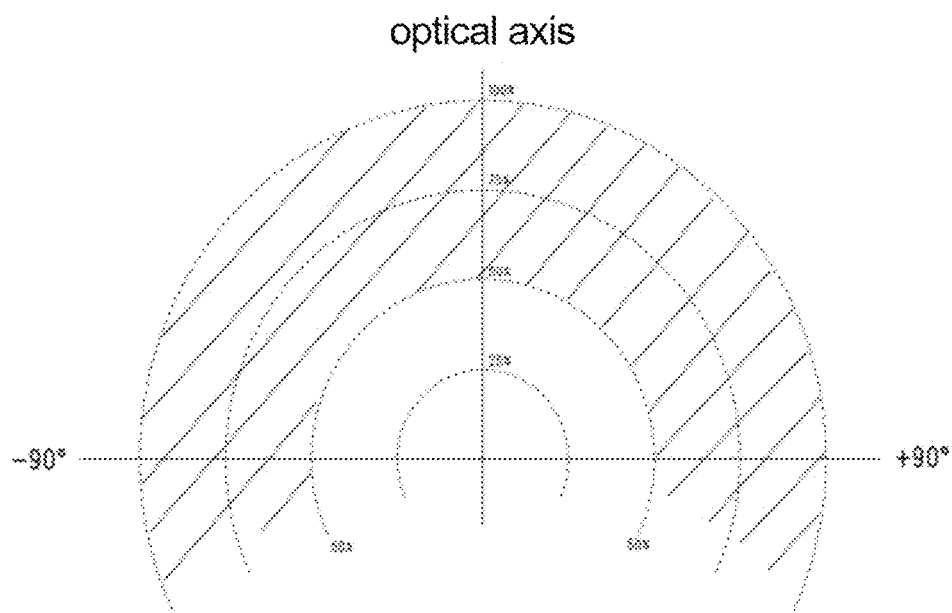
FIG. 1 shows a requirement profile for the homogeneity of the illumination of the field of view of the objective.
Figure 2:
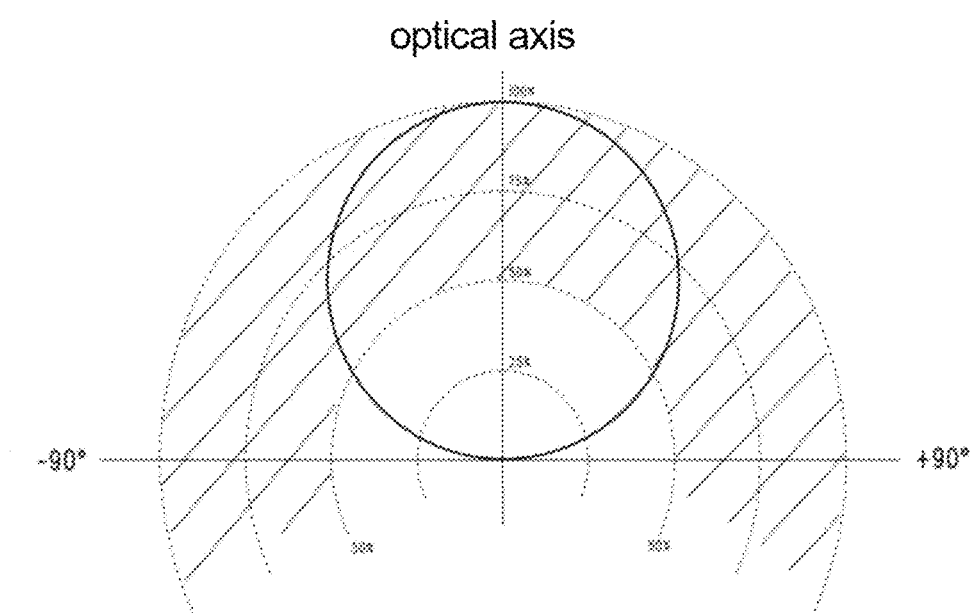
FIG. 2 shows how a Lambertian emitter illuminates the field of view according to the prior art.
Figure 15:
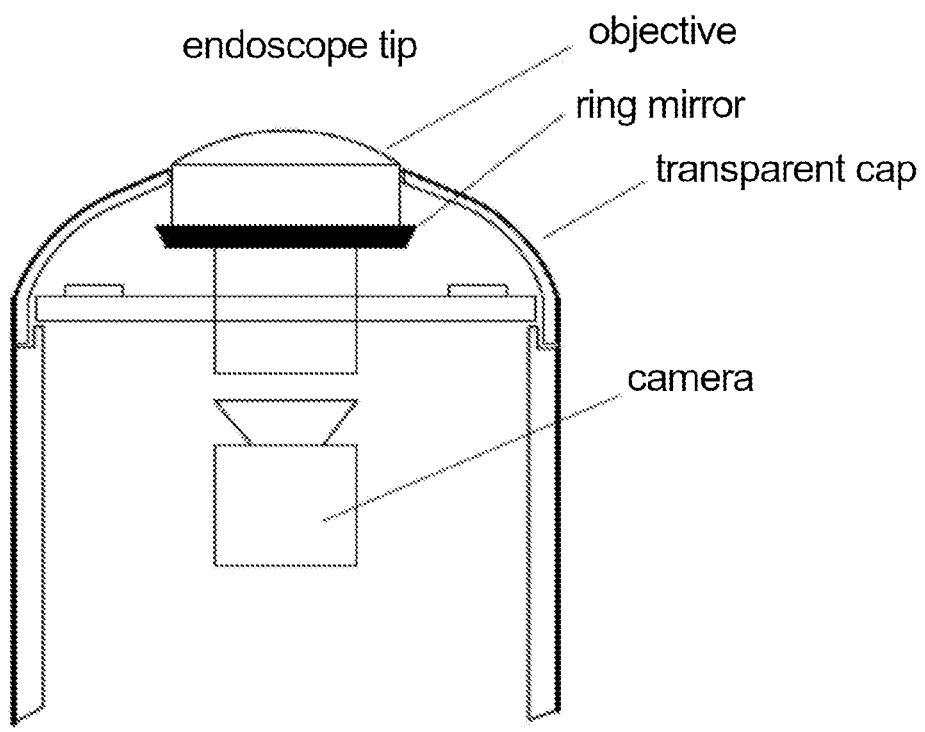
FIG. 15 shows an endoscope tip according to a second example of the invention.
Figure 16:
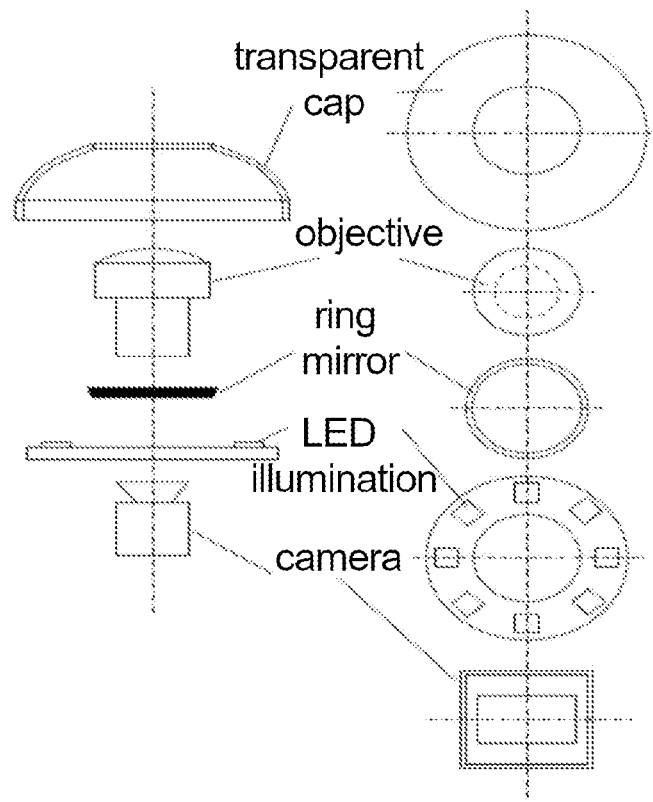
FIG. 16 shows cross-sections and plan views of components of the endoscope tip according to FIG. 15.

In some examples of the invention, both the emission direction of the LEDs is inclined with respect to the optical axis of the objective (as in FIG. 1*i*) and a ring mirror is mounted around the objective (as in FIG. 15). In addition, a part of the outer shell of the objective can also be coated reflectively, as in the third example. The illumination in the outer field of view can thereby be improved even further.

In so far as the outer shell of the objective is not coated reflectively, it may be black, so that it reflects almost no light.

The reflective surfaces can be formed by metallic coating, for example with silver. Alternatively, in a case where the space between the cap, the outer shell of the objective and the mounting surface of the LEDs is filled with a transparent dielectric, a reflective surface can also be formed by another dielectric with lower refractive index. Further, in this case, the cap can be identical to an outer layer of the transparent dielectric.

According to a fourth example of the invention, an optically refractive element is mounted in the space between the LEDs and the cap to direct a part of the light into the outer field of view. For example, the optically refractive element can lie directly on an outer part of the light emitting surface of the LED and, in a cross-section, extend outwardly in a wedge-shaped manner. When the light from the LED emerges from the wedge-shaped optically refractive element, it is deflected outwards, towards the outer field of view.

The optically refractive elements of the LEDs can be connected so that they form a truncated cone surface, wherein the axis of the truncated cone preferably (but not necessarily) coincides with the optical axis of the objective. The optically refractive element of the fourth example can also be combined with one or more of the first to third examples.

FIGS. 21 and 22 illustrate a general principle according to some examples of the invention. They each show a cross-section of a (hypothetical or real) endoscope tip in a plane spanned by the optical axis 11 of the objective 1 and the light emission axis of at least one of the LEDs 2. The LEDs 2 emit the (hypothetical or real) emission light 20 symmetrically to the light emission axis.

FIG. 21 shows a hypothetical reference configuration corresponding to FIG. 4 according to the prior art. In the reference configuration, the LEDs 2 are arranged in a plane perpendicular to the optical axis 11 of the objective 1. The LEDs 2 emit (hypothetical) emission light 20 parallel to the direction of the optical axis 11. The (hypothetical) emission light 20 falls directly, i.e. without being deflected by other components, such as mirrors or optically refractive elements (lenses), onto the transparent cap 6. There, it is possibly deflected and emitted as hypothetical illumination light 6*o* into the object space (or into the field of view) of the objective 1. The hypothetical illumination light is based exclusively on emission light emitted directly by the LEDs 2 onto the cap 6. The dashed lines indicate that the reference configuration is a hypothetical configuration.

A real configuration according to some examples of the invention is shown for comparison in FIG. 22. The real configuration differs from the reference configuration in that one or both of the following conditions are satisfied:
 The emission light 20 is emitted by the LEDs 2 not parallel to the optical axis 11; and
 The (real) illumination light 61 is based at least in part on emission light that has not been emitted directly by at least one LED 2 onto the cap 6, but has been deflected by a reflective or refractive element.

Otherwise, the real configuration of FIG. 21 is functionally identical to the hypothetical configuration of FIG. 22. In particular, the exit point of the respective light emission axis from the LEDs 2 is at the same position.

FIG. 22 shows an example in which the emission light 20 is emitted not parallel to the optical axis. In addition, by there being a gap between the emission light 20 and the illumination light 61, it is indicated that the illumination light contains components other than those emitted directly by the LEDs 2 onto the cap 6.

As can be seen from FIG. 22, the real illumination light 61 is directed further away from the optical axis than the hypothetical illumination light 60.

The arrows 20 symbolizing the emission light of the LEDs 2 indicate the centroid of the angular distribution of the emission light. Typically, the emission light is emitted symmetrically about this centroid (e.g. Lambertian emitter). The arrows 60 and 61 symbolizing the (hypothetical or real) illumination light indicate the centroid of the angular distribution of the respective illumination light. Generally, the angular distribution of the illumination light is not necessarily symmetrical about this arrow because of the shadowing by the objective and, in the case of the real illumination light 61, possibly also because of the reflected or optically refracted or optically diffracted components of the illumination light. An LED is an example of a light emitting device (also referred to as a "light emitter" according to some examples of the invention. Instead of an LED, for example, also an emission end of a light guide can be used. Also some of the light emitting devices can be LEDs and others of the light emitting devices can be emission ends of light guides.

An objective is understood to mean a lens or a system of lenses and possibly further optical elements imaging a scene onto an image surface. In particular, an objective images the scene continuously onto the image surface. This means that points adjacent in the scene are also adjacent in the image on the image surface. The angle of view of the objective is greater than 180°. It is preferably greater than 200°, more preferably greater than 220°, and even more preferably greater than 230°. Such objectives are described, for example, in EP3767363 A1. Typically, the endoscope tip includes a single objective.

The endoscope may be a rigid endoscope in which the proximal end of the endoscope tip is connected to a rigid tube. The endoscope may be a flexible endoscope in which the proximal end of the endoscope tip is connected to a flexible tube. Both the rigid tube and the flexible tube are referred to as a "shaft". The connection of the endoscope tip to the shaft can be effected directly or indirectly by means of an angulation element. The endoscope may be a freely floating endoscope (capsule endoscope) which does not have a shaft. The endoscope (and thus, of course, also the endoscope tip) may be suitable for insertion into a cavity of a human body, such as, for example, a bronchoscope, a laryngoscope, or a coloscope.

The invention claimed is:

1. An endoscope tip or capsule endoscope comprising:
an objective lens for imaging a field of view; and
a light for illuminating the field of view with illumination light, wherein
the objective lens has an optical axis;
the objective lens has an angle of view greater than 180°;
the light is arranged around the objective lens in a plan view along the optical axis;
the light comprises a transparent cap from which the illumination light is emitted into the field of view;
the light comprises one or more light emitters configured to emit respective emission light from a respective light emitting surface; and
the light comprises a mirror that reflects without diffusion at least a part the light from of one of the emission lights in a direction further away from the direction of the optical axis than a direction in which the part of the light from one of the emission lights is incident on the mirror, such that an angle of illumination of the illumination light is greater than or equal to that of the field of view of the objective lens.

2. The endoscope tip or capsule endoscope according to claim 1, wherein the mirror comprises, for each of the light emitters, a respective reflective surface that reflects at least a part of the respective emission light in a respective direction further away from the direction of the optical axis than a respective direction in which the part of the respective emission light is incident on the respective reflective surface.

3. The endoscope tip or capsule endoscope according to claim 2, wherein the light is rotationally symmetric about a rotation axis.

4. The endoscope tip or capsule endoscope according to claim 3, wherein
the light is arranged such that the rotation axis is identical to the optical axis.

5. The endoscope tip or capsule endoscope according to claim 1, wherein
the mirror is a ring mirror.

6. The endoscope tip or capsule endoscope according to claim 5, wherein
the axis of the ring mirror is identical to the optical axis.

7. The endoscope tip or capsule endoscope according to claim 1, wherein an angular distribution of the illumination light in a plane containing the optical axis comprises an angular range of more than 90°.

8. The endoscope tip or capsule endoscope according to claim 1, wherein each of the light emitters is a light emitting diode or an emission end of a light guide.

9. The endoscope tip or capsule endoscope according to claim 1, wherein
the objective lens is located at the distal end of the endoscope tip;
the light emitters are arranged in a plane perpendicular to the optical axis; and
the arrangement plane is farther from the distal end of the endoscope tip than an apex of a lens of the objective lens closest to the field of view of the objective lens.

10. The endoscope tip or capsule endoscope according to claim 9, wherein
an outer shell of the objective lens has a protrusion arranged closer to the distal end than the light emitters in the direction of the optical axis;
a bottom surface of the protrusion facing the light emitters and at least a part of the outer shell adjoining the bottom surface of the protrusion in the proximal direction are coated reflectively.

11. The endoscope tip or capsule endoscope according to claim 1, wherein the objective lens is the only objective lens present in the endoscope tip.

12. An endoscope comprising:
an endoscope tip comprising:
an objective lens for imaging a field of view; and
a light for illuminating the field of view with illumination light, wherein
the objective lens has an optical axis;
the objective lens has an angle of view greater than 180°;
the light is arranged around the objective lens in a plan view along the optical axis;
the light comprises a transparent cap from which the illumination light is emitted into the field of view;

the light comprises one or more light emitters configured to emit respective emission light from a respective light emitting surface; and the light comprises a mirror that reflects without diffusion at least a part the light from of one of the emission lights in a direction further away from the direction of the optical axis than a direction in which the part of the light from one of the emission lights is incident on the mirror, such that an angle of illumination of the illumination light is greater than or equal to that of the field of view of the objective lens; and a shaft whose distal end is directly connected to a proximal end of the endoscope tip.

13. An endoscope comprising:

an endoscope tip comprising:

an objective lens for imaging a field of view; and a light for illuminating the field of view with illumination light, wherein the objective lens has an optical axis;

the objective lens has an angle of view greater than 180°;

the light is arranged around the objective lens in a plan view along the optical axis;

the light comprises a transparent cap from which the illumination light is emitted into the field of view;

the light comprises one or more light emitters configured to emit respective emission light from a respective light emitting surface; and the light comprises a mirror that reflects without diffusion at least a part the light from of one of the emission lights in a direction further away from the direction of the optical axis than a direction in which the part of the light from one of the emission lights is incident on the mirror, such that an angle of illumination of the illumination light is greater than or equal to that of the field of view of the objective lens; and a shaft having a distal end indirectly connected to a proximal end of the endoscope tip.

* * * * *